United States Patent [19]

Eckenhoff et al.

[11] Patent Number: 4,612,186

[45] Date of Patent: * Sep. 16, 1986

[54] METHOD FOR ESTABLISHING BLOOD LEVELS OF BIOCIDE IN ANIMALS

[75] Inventors: James B. Eckenhoff, Los Altos; Richard Cortese, Los Gatos; Felix A. Landrau, Milpitas, all of Calif.

[73] Assignee: ALZA Corporation, Palo Alto, Calif.

[ * ] Notice: The portion of the term of this patent subsequent to Jun. 17, 2003 has been disclaimed.

[21] Appl. No.: 780,863

[22] Filed: Sep. 27, 1985

Related U.S. Application Data

[63] Continuation-in-part of Ser. No. 590,778, Mar. 19, 1984.

[51] Int. Cl.$^4$ .................... A61K 9/00; A61K 9/20
[52] U.S. Cl. ......................... 424/15; 424/14; 604/890; 604/892
[58] Field of Search ............ 424/14, 15; 604/890, 604/892

[56] References Cited

U.S. PATENT DOCUMENTS

| | | | |
|---|---|---|---|
| 2,340,037 | 1/1944 | Zipper | 167/83 |
| 3,594,469 | 7/1971 | Whitehead et al. | 424/22 |
| 3,732,865 | 5/1973 | Higuchi et al. | 128/260 |
| 3,760,804 | 9/1973 | Higuchi et al. | 128/260 |
| 3,769,805 | 9/1973 | Higuchi | 128/260 |
| 3,844,285 | 10/1974 | Laby | 128/260 |
| 3,845,770 | 11/1974 | Theeuwes et al. | 128/260 |
| 3,929,132 | 12/1975 | Higuchi | 128/260 |
| 3,995,631 | 12/1976 | Higuchi et al. | 604/893 |
| 3,995,632 | 12/1976 | Nakano et al. | 128/260 |
| 4,034,756 | 7/1976 | Higuchi et al. | 128/260 |
| 4,088,864 | 5/1978 | Theeuwes et al. | 219/121 |
| 4,111,202 | 9/1978 | Theeuwes | 604/893 |
| 4,178,361 | 12/1979 | Cohen et al. | 424/22 |
| 4,196,187 | 4/1980 | Dannelly et al. | 424/21 |
| 4,200,098 | 4/1980 | Ayer et al. | 128/260 |
| 4,228,149 | 10/1980 | Brewer et al. | 424/21 |
| 4,235,236 | 11/1980 | Theeuwes | 128/260 |
| 4,285,987 | 8/1981 | Ayer et al. | 427/3 |
| 4,468,220 | 8/1984 | Willbanks | 604/890 |

FOREIGN PATENT DOCUMENTS

| | | |
|---|---|---|
| 499029 | 3/1972 | Australia . |
| 2729068 | 11/1979 | Fed. Rep. of Germany . |
| 1540258 | 9/1968 | France . |

*Primary Examiner*—Ronald W. Griffin
*Attorney, Agent, or Firm*—Paul L. Sabatine; Edward L. Mandell; Steven F. Stone

[57] ABSTRACT

A dispensing device is disclosed for delivering a beneficial agent. The device comprises (1) a semipermeable housing defining an internal space, (2) a dense member in the space, (3) a heat responsive composition containing a beneficial agent in the space, (4) an expandable member in the space, and (5) a passageway in the semipermeable housing for delivering the beneficial agent from the dispensing device.

15 Claims, 14 Drawing Figures

METHOD FOR ESTABLISHING BLOOD LEVELS OF BIOCIDE IN ANIMALS

CROSS-REFERENCE TO RELATED APPLICATION

This application is a continuation-in-part of U.S. patent application Ser. No. 06/590,778 filed on Mar. 19, 1984.

FIELD OF THE INVENTION

This invention pertains to both novel and useful delivery system. More particularly, the invention relates to a delivery system comprising a semipermeable wall that surrounds, in at least a part, a reservoir, or an inner hollow body member housing a thermo-responsive beneficial agent formulation, an expandable driving member, and a density member. The members comprising the delivery system perform in unison for delivering the beneficial agent at a controlled rate to a ruminant environment of use over a prolonged period of time. The invention pertains also to a plurality of laminated structures used for manufacturing the delivery system, and to methods for treating infestations.

BACKGROUND OF THE INVENTION

Ruminant animals, including cattle, sheep, giraffe, deer, goat, bison and camels, and more particularly cattle and sheep, comprise an important group of animals that require periodic administration of medicines and nutrients. The medicines and nutrient are administered for the treatment and alleviation of various conditions, and for better health. Ruminants have a complex three or four compartment stomach.

The rumen, the largest of the stomach compartments, serves as an important location for receiving and passing medicines and nutrients into other compartments, including the abomasum and the intestine.

Presently, ruminants are treated by repeated administrations of medicines and nutrients at frequent time intervals. This form of treatment is inconvenient and expensive, and it does not lend itself to good reliable therapy.

Additionally, medicines and nutrients are orally administered in the form of a bolus to ruminants. However, this form of therapy, like the repeated dose mode of administration, also does not lend itself to acceptable therapy. That is, ruminants regurgitate what they swallow, they chew their cuds, and they spit out conventional boluses quickly after administration.

There is, therefore, in view of the above presentation, a pressing need for use in ruminant therapy for a therapeutic delivery system that after a single administration, efficiently administers medicines and nutrients over a prolonged period of time. There is also a pressing need for a therapeutic delivery system for prolongedly releasing a medicine or a nutrient at a controlled rate in the rumen, by a delivery system that is easily swallowed by the ruminant and remains in the rumen for a long period of time without being regurgitated or otherwise eliminated from the rumen.

OBJECTS OF THE INVENTION

Accordingly, it is a principle object of this invention to provide both a novel and useful therapeutic delivery system for use in ruminant therapy that fulfills the pressing need known to the prior art.

Another object of the invention is to provide a therapeutic delivery system for use in ruminants that delivers a medicine or a nutrient at a controlled rate over a prolonged period of time.

Another object of the invention is to provide a therapeutic delivery system that can remain in the rumen of a ruminant for a prolonged period of time.

Another object of the invention is to provide a therapeutic delivery system manufactured in the form of a drug dispensing device that is self-contained, self-starting and self-powered in a fluid environment, is easy to make, and can be used for dispensing beneficial agents to a warm-blooded animal.

Yet another object of the invention is to provide a drug delivery system comprising an internal capsule arrangement that makes it easier to manufacture the system at a lesser cost thereby increasing the usefulness of the system particularly for domestic animals.

Yet another object of the invention is to provide a drug delivery system comprising a capsule lumen containing a temperature-sensitive composition, an expandable member and a densifier in optional parallel arrangement, an outer semipermeable wall surrounding the capsule, and a dispensing passageway useful for dispensing a beneficial agent to an animal.

Yet another object of the invention is to provide a drug delivery device comprising a semipermeable wall that surrounds in at least a part an internal lumen and which delivery device delivers a thermo-sensitive composition containing a beneficial agent by the combined physical-chemical operations of the composition melting and becoming fluid to semisolid, or the like, with the composition being displaced from the device by an expanding member that swells and occupies space in the area initially occupied by the compartment.

Another object of the invention is to provide a drug delivery system comprising a dense member for keeping the delivery system in the rumen over time wherein the delivery system administers a composition that is a complete pharmaceutical dosage regimen for a prolonged period of time, the use of which delivery system requires intervention only for the initiation of the regimen.

Yet another object of the invention is to provide a drug delivery system that can deliver a beneficial drug contained in a thermo-responsive, lipophilic pharmaceutically acceptable carrier that melts in the rumen in the presence of thermal energy absorbed from the rumen environment of use into the dispensable composition that is innocuous, thereby substantially avoiding mammalian tissue irritation and interaction with mammalian protein tissues.

Yet another object of the invention is to provide a drug delivery system containing an eutectic composition formed of at least two components and at least one drug, which eutectic composition has a melting point approximately the same as the temperature of a warm-blooded animal's rumen, and is dispensed from the delivery system at said temperature.

Yet another object of the invention is to provide a delivery system comprising an inner placed capsule housing a thermo-responsive hydrophilic or hydrophobic composition comprising insoluble to soluble drugs, and which thermo-responsive composition in response to energY input present in the gastrointestinal tract of a ruminant, changes its form and becomes dispensable for operative delivery from the delivery system.

Yet another object of the invention is to provide a drug delivery system for dispensing a drug to a ruminant, which delivery system comprises an inner capsule body containing a thermoplastic composition, an expandable component, and a dense member, and which composition includes a beneficial agent that is insoluble in an aqueous environment and can be housed in the delivery system in a nonaqueous dispensing carrier that can be delivered to a ruminant.

Other objects, features and advantages of the invention will be more apparent to those skilled in the dispensing art from the following detailed description of the specification, taken in conjunction with the drawings and the accompanying claims.

BRIEF DESCRIPTION OF THE DRAWINGS

In the drawings, which are not drawn to scale, but are set forth to illustrate various embodiments of the invention, the drawing figures are as follows.

DETAILED DESCRIPTION OF THE DRAWINGS

Figure 1:
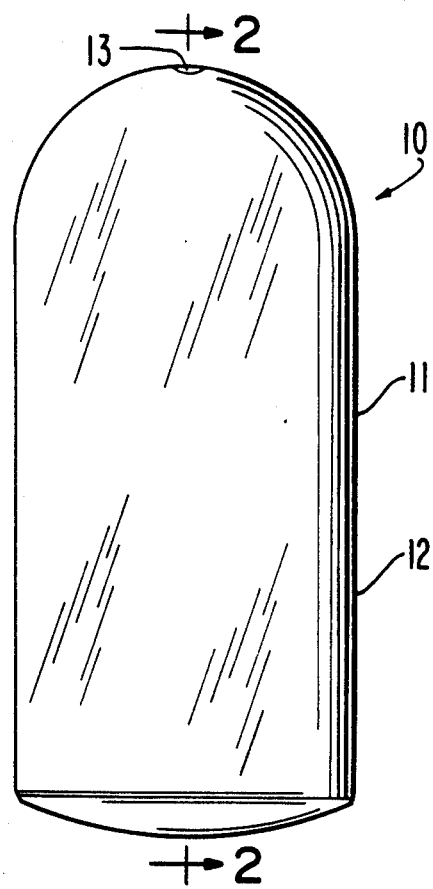
FIG. 1 is a view of a delivery system designed and manufactured for orally administering a beneficial agent to a warm-blooded ruminant animal.

Turning now to the drawing figures in detail, which are examples of new and useful therapeutic delivery system for dispensing a beneficial agent, and which examples are not to be construed as limiting, one example of a dispenser is depicted in FIG. 1, identified by the numeral 10. In FIG. 1, delivery system 10 comprises a body 11 formed of wall 12 that surrounds and defines an internal lumen, not seen in FIG. 1. Therapeutic system 10 comprises a passageway 13, indicated by a partial hole, for delivering a beneficial agent from system 10.

Figure 2:
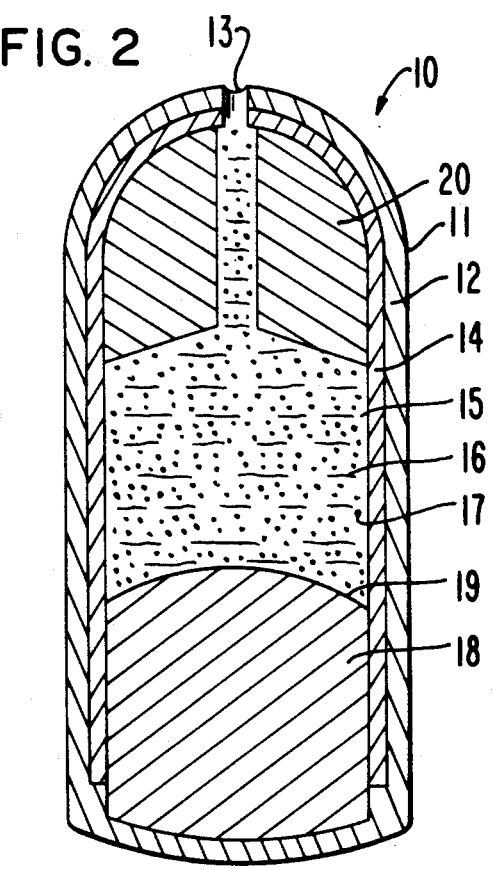
FIG. 2 is an opened view of the delivery system of FIG. 1, through 2—2 the vertical length of the delivery system for illustrating the structure of the delivery system comprising initially an outside wall, an inside wall, a thermo-responsive composition, an expandable member and a dense member.

FIG. 2 is an opened view of therapeutic dispenser system 10 of FIG. 1. Therapeutic system 10 of FIG. 2 comprises body 11 and wall 12 and at least one or a plurality of preformed or formed during operation of dispenser 10 passageway 13. Wall 12 surrounds internal capsule wall 14 and internal compartment or lumen 15. Wall 12 is formed in a presently preferred embodiment of a semipermeable wall forming composition that is substantially permeable to the passage of an external fluid, and it is substantially impermeable to the passage of a beneficial agent and other ingredients contained in system 10. In another embodiment semipermeable wall 12 can partly surround the capsule and the rest of the wall can be of a different composition. Wall 12 is nontoxic and it maintains its physical and chemical integrity, that is, it does not erode during the dispensing period. System 10 is a preferred embodiment comprising internal capsule wall 14 made in its final manufacture as a single unit capsule body member. That is, capsule wall 14 cannot easily be separated into part. Further in FIG. 2, capsule wall 14 surrounds lumen 15. Lumen 15 contains a thermo-responsive heat sensitive composition 16, identified by wavy lines, containing a beneficial agent 17, represented by dots. Lumen 15 further contains an expandable driving member 18 that is in layered contact with a contacting surface 19 of thermo-responsive composition 16. Both thermo-responsive composition 16 and expandable member 18 have a shape that corresponds to the internal shape of capsule wall 14 and lumen 15. Lumen 15 also contains a dense member 20 or densifier that is in contact with thermo-responsive composition 16, which dense member 20 is positioned in lumen 15 distant from expandable member 18. A passageway 13 extends through dense member 20 for delivering beneficial agent 17 from system 10. Passageway 13 extends through outer semipermeable wall 12 and internal capsule wall 14 for completing communication between lumen 15 and the exterior of system 10. Dense member 20 is an important component of delivery system 10 for keeping system 10 in the rumen of an animal over a prolonged period of time. In another manufacturing embodiment, the beneficial agent formulation layer 16 and 17, comprising heat sensitive composition 16 and beneficial agent 17 of system 10 can alternately be heterogeneous in composition versus homogeneous. Beneficial agent formulation layer 16 and 17 can be comprised of a subset of multiple individual beneficial agent formulation layers for providing pulses of beneficial agent over the delivery duration of system 10. The individual beneficial agent formulation layers can, for example, be lipophilic and thermo-responsive in nature and are separated by spacer elements which are, for example, lipophilic to hydrophilic and thermo-responsive in nature, but contain no beneficial agent.

Figure 3:
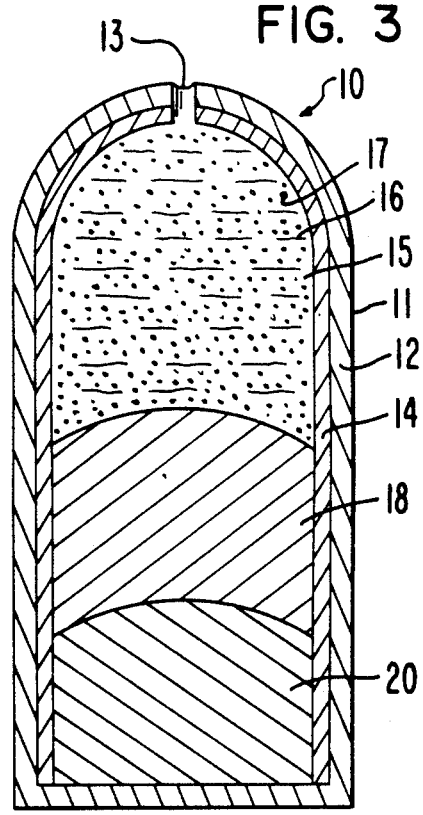
FIG. 3 is an opened view through 2—2 of FIG. 1, the vertical length of the delivery system, for illustrating another embodiment similar to the embodiment in FIG. 2.

FIG. 3 depicts another manufacture provided by the invention. FIG. 3 is an opened view of the dispensing system 10 of FIG. 1, and it comprises body 11 an exterior wall 12 of uniform thickness, internal wall 14, internal compartment 15, and passageway 13. System 10 further comprises a thermo-responsive heat composition 16 containing beneficial agent 17. Thermo-responsive heat composition 16 is, in this manufacture, immediately adjacent to passageway 13. Compartment 15 also contains an expandable driving member 18 in laminar arrangement with thermo-heat responsive compotosition 16. Driving member 18 also is in laminar arrangement with, and positioned adjacent to dense member 20. Dense member 20 in FIG. 3 is positioned distant from passageway 13.

The rumen-retentive delivery system 10 can be manufactured in a variety of sizes and shapes for administering system 10 to ruminant animals. One presently preferred shape is a cylinder-like or capsule-like shape. For example, for use with sheep, delivery system 10 can embrace a capsule-like shape and have a diameter of about 0.5 inches to 1 inch (1.3 cm to 2.5 cm) and a length of about 0.5 inches to 2.5 inches (1.3 cm to 6.6 cm). For use with cattle, system 10 has a diameter of about 0.5 inches to 1.5 inches (1.3 cm to 3.8 cm), and a length of about 1 inch to 3.5 inches (2.5 cm to 7.8 cm).

Figure 4:
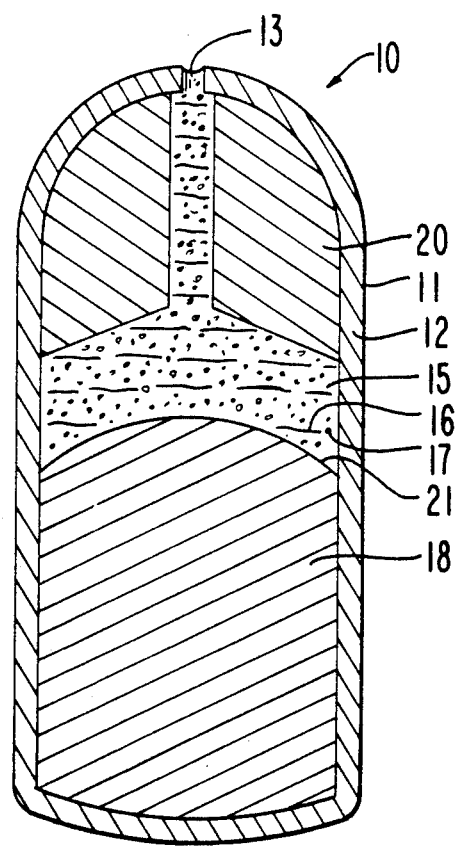
FIG. 4 is an opened view of the delivery system depicting a semipermeable wall surrounding a lumen with the delivery system in operation with all the elements of the delivery system acting in concert for the controlled delivery of a beneficial agent over time.
Figure 5:
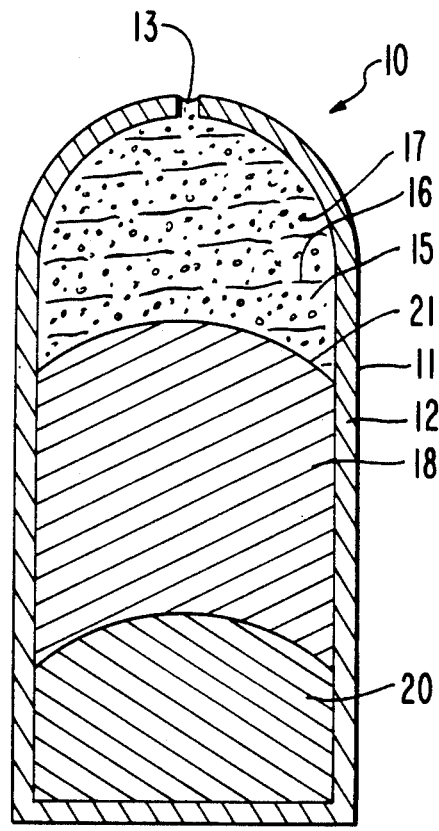
FIG. 5 is an opened view of a delivery system depicting the system in operation, as described in respect to FIG. 4.

Therapeutic delivery system 10 of FIGS. 1, 2 and 3 in operation delivers beneficial agent 17 to the fluidic environment of use by a combination of thermodynamic and kinetic integrally performed activities. That is, in operation, heat sensitive composition 16 in response to the temperature of the rumen absorbs energy, melts and forms a fluidic or a semipaste like deliverable composition for delivering agent 17 through passageway 13. As composition 16 melts, concomitantly external fluid is imbibed through external semipermeable wall 12 by expandable hydrophilic layer 18 in a tendency towards osmotic equilibrium, as seen in FIG. 4 and FIG. 5, to continuously expand and swell layer 18. Layer 18 expands, in a preferred embodiment, while maintaining an intact immiscible boundary at interface 21 defined by heat-sensitive composition 16 and expandable layer 18. The expansion and swelling of layer 18 increases the volume of layer 18 and simultaneously layer 18 expands in compartment 15, as seen in FIGS. 4 and 5, thereby urging composition 16 through passageway 13. Further in operation, as fluid is imbibed into device 10, in the embodiment wherein internal wall 14 is formed of a thin-walled, water-soluble gelatin capsule that dissolves at a body temperature of 37° C., the capsule softens and dissolves leaving system 10 with semipermeable wall 12. The dissolved gelatin blends with composition 16, and in some instances lubricates the inside surface of wall 12. Dense member 19 maintains delivery system 10 in the rumen thereby enabling delivery system 10 to deliver beneficial agent 17 at a controlled rate over a prolonged period of time, usually about 1 day to about 6 months, or longer.

Figure 6:
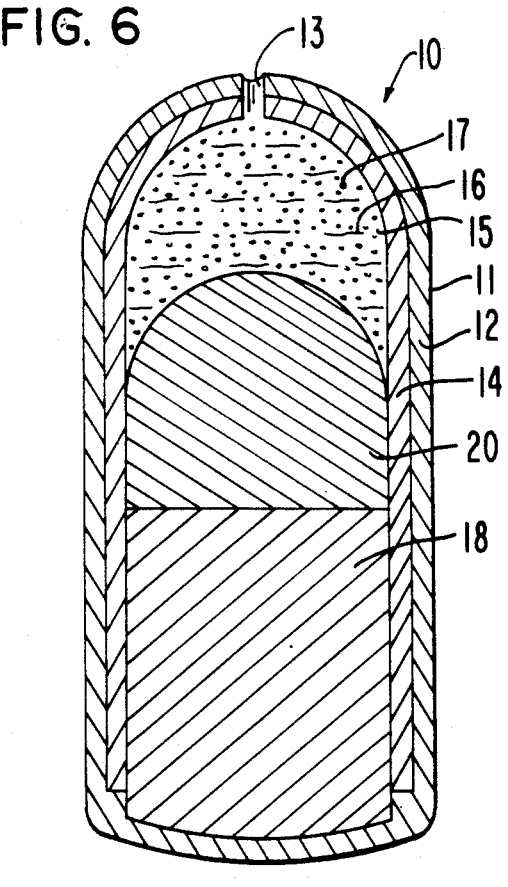
FIG. 6 is an opened view of a delivery system provided by the invention depicting a different internal structural configuration for the elements comprising the delivery system.

FIG. 6 is an opened view of delivery system 10 depicting yet a different internal laminated arrangement of the members forming system 10. In FIG. 6, system 10 comprises heat-sensitive lamina 16 immediately adjacent to passageway 13, expandable lamina 18 positioned distant from passageway 13, and also distant from heat-responsive lamina 16, and a dense lamina 20 positioned between heat-responsive lamina 16 and expandable lamina 18.

Figure 7:
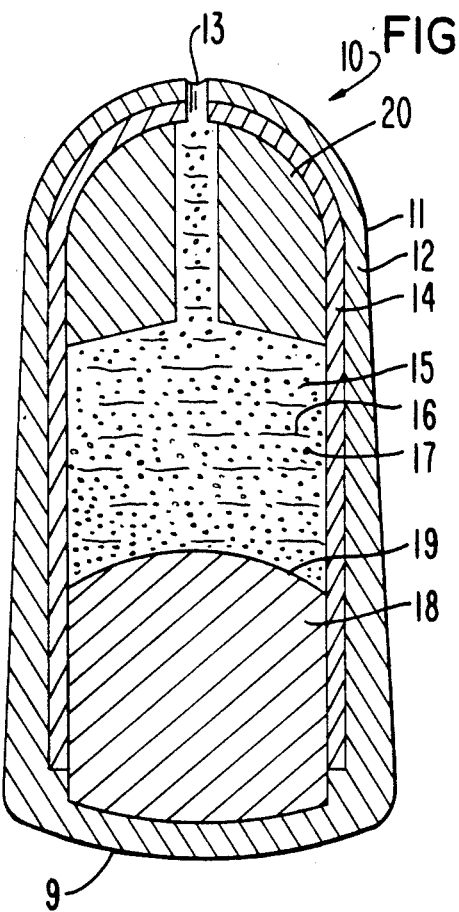
FIG. 7 is an opened view of a delivery system provided with an exterior wall of varying thickness.
Figure 8:
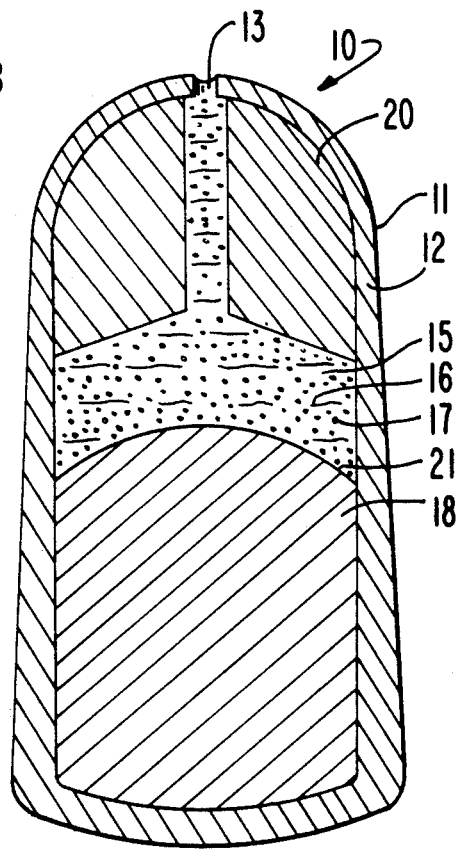
FIG. 8 is an opened view of the delivery system of FIG. 7 in operation delivering a beneficial agent over time.

FIG. 7 is an opened view of delivery system 10 depicting delivery system 10 comprising the internal structure identified previously. In FIG. 7, delivery system 10 is provided with an external semipermeable wall 12 of varying thickness. In the embodiment illustrated, wall 12, increases in thickness from the top of delivery system 10 near passageway 13 towards bottom 9 of delivery system 10. By providing delivery system 10 with semipermeable wall 12 of varying thickness, the invention provides a multiplicity of drug delivery programs and patterns. Delivery system 10, of FIG. 7 in operation, as depicted in FIG. 8 and in the manner previously described, with internal wall 14 of FIG. 8 lubricating the inside surface of wall 12 as accompanied by the outward and upward expansion of members 16 and 18.

Figure 9:
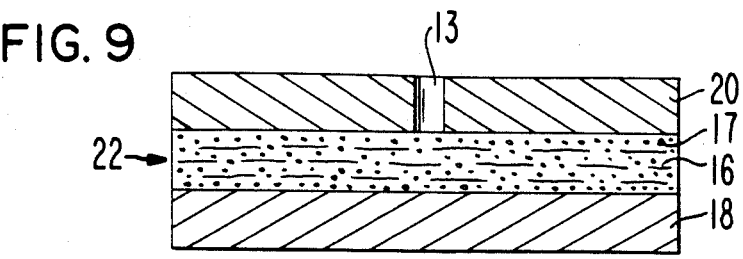
FIG. 9 illustrates a cross-section of a laminate provided by the invention comprising a dense lamina, a heat-responsive lamina and an expandable lamina.

FIG. 9 is an opened view of a laminated structure corresponding to the internal arrangement depicted for delivery system 10 of FIG. 2. In FIG. 9, the three-layered laminate 22 comprises a dense lamina 20, a heat-responsive lamina 16 and an expandable lamina 18. Dense lamina 20 has a passageway 13 therethrough for communicating with lamina 16. Lamina 16 contains beneficial agent 17.

Figure 10:
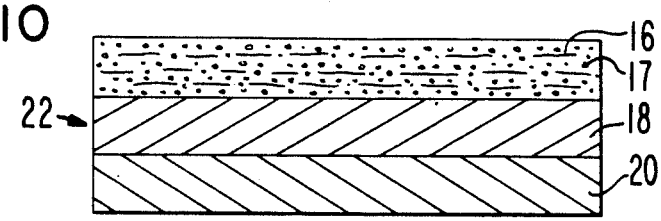
FIG. 10 illustrates a cross-section of another laminate comprising a heat-responsive lamina, an expandable lamina and a dense lamina.

FIG. 10 is a tri-lamina in opened view that depicts the laminated arrangement used for manufacturing system 10 of FIG. 3. In FIG. 10 tri-lamina 22 comprises heat-responsive lamina 16 containing beneficial agent 17 laminated to expandable lamina 18, which later lamina 18 is laminated to dense lamina 20.

Figure 11:
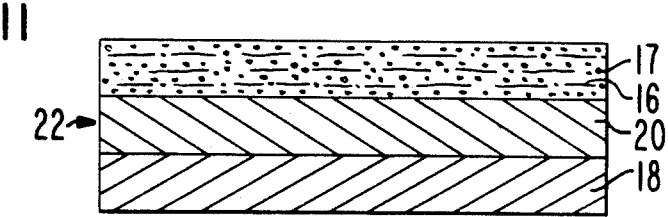
FIG. 11 illustrates a cross-section of another lamina provided by the invention comprising a heat-responsive lamina, a dense lamina and an expandable lamina.

FIG. 11 depicts an opened cross-section laminate 22. Laminate 22 illustrates the structure of FIG. 6 comprising a dense lamina 20 position between and in contacting arrangement with a heat-responsive lamina 16 containing agent 17 and an expandable lamina 18.

While FIGS. 1 through 11 illustrate various delivery systems 10 that can be made according to the invention, it is to be understood these systems are not to be construed as limiting the invention, as the dispenser can take other shapes, sizes and forms for delivering beneficial agents to the biological environment of use. The delivery system can be used in veterinary clinics, farms, zoos, laboratories, on the range, in feed lots and other environments of use.

DETAILED DESCRIPTION OF THE INVENTION

In accordance with the practice of this invention, it has now been found that internal wall 14 of delivery system 10 can be made as a capsule member. The capsule member generally is tubular shaped and it has a mouth at one end, and at the end distant therefrom it is closed in a hemispherical or dome shaped end. The capsule member serves as a hollow body having a wall that surrounds and defines an interior compartment provided with an opening for establishing communication with the exterior of the capsule and for filling the capsule.

In one embodiment, a capsule is made by dipping a mandrel, such as a stainless-steel mandrel, into a bath containing a solution of a capsule wall forming material to coat the mandrel with the material. Then, the mandrel is withdrawn, cooled, and dried in a current of air. The capsule is stripped from the mandrel and trimmed to yield a capsule with an internal lumen.

The materials used for forming the capsule are the commercially available materials including gelatin, gelatin having a viscosity of 15 to 30 millipoises and a bloom strength up to 150 grams; gelatin having a bloom value of 160 to 250; a composition comprising gelatin, glycerine water and titanium dioxide; a composition comprising gelatin, erythrosin, iron oxide and titanium dioxide; a composition comprising gelatin, glycerine, sorbitol, potassium sorbate and titanium dioxide; a composition comprising gelatin, acacia, glycerin and water; water soluble polymers that permit the transport of water therethrough and can be made into capsules, and the like.

Representative materials for forming the semipermeable wall 12 include semipermeable homopolymers, semipermeable copolymers, and the like. In one embodiment typical materials include cellulose esters, cellulose monoesters, cellulose diesters, cellulose triesters, cellulose ethers, and cellulose ester-ethers, mixtures thereof, and the like. These cellulosic polymers have a degree of substitution, D.S., on their anhydroglucose unit from greater than 0 up to 3 inclusive. By degree of substitution is meant the average number of hydroxyl groups originally present on the anhydroglucose unit that are replaced by a substituting group, or converted into another group. The anhydroglucose unit can be partially or completely substituted with groups such as acyl, alkanoyl, aroyl, alkyl, alkenyl, alkoxy, halogen, carboalkyl, alkylcarbamate, alkylcarbonate, alkylsulfonate, alkylsulfamate, and like semipermeable polymer forming groups.

The semipermeable materials typically include a member selected from the group consisting of cellulose acylate, cellulose diacylate, cellulose triacylate, cellulose acetate, cellulose diacetate, cellulose triacetate, mono-, di- and tri-cellulose alkanylates, mono-, di- and tri-alkenylates, mono-, di- and tri-aroylates, and the like. Exemplary polymers including cellulose acetate having a D.S. of 1.8 to 2.3 and an acetyl content of 32 to 39.9%; cellulose diacetate having a D.S. of 1 to 2 and an acetyl content of 21 to 35%; cellulose triacetate having a D.S of 2 to 3 and an acetyl content of 34 to 44.8%, and the like. More specific cellulosic polymers include cellulose propionate having a D.S. of 1.8 and a propionyl content of 38.5%; cellulose acetate propionate having an acetyl content of 1.5 to 7% and an acetyl content of 39 to 42%; cellulose acetate propionate having an acetyl content of 2.5 to 3%, an average propionyl content of 39.2 to 45% and a hydroxyl content of 2.8 to 5.4%; cellulose acetate butyrate having a D.S. of 1.8, an acetyl content of 13 to 15%, and a butyryl content of 34 to 39%; cellulose acetate butyrate having an acetyl content of 2 to 29,5%, a butyryl content of 17 to 53%, and a hydroxyl content of 0.5 to 4.7%; cellulose triacylates having a D.S. of 2.9 to 3 such as cellulose trivalerate, cellulose trilaurate, cellulose tripalmitate, cellulose trioctanoate, and cellulose tripropionate; cellulose diesters having a D.S. of 2.2 to 2.6 such as cellulose disuccinate, cellulose dipalmitate, cellulose dioctanoate, cellulose dicarpylate; cellulose propionate morpholinobutyrate; cellulose acetate butyrate; cellulose acetate phthalate, and the like; mixed cellulose esters such as cellulose acetate valerate, cellulose acetate succinate, cellulose propionate succinate, cellulose acetate octanoate, cellulose valerate palmitate, cellulose acetate heptonate, and the like. Semipermeable polymers are known in U.S. Pat. No. 4,077,407, and they can be made by procedures described in *Encyclopedia of Polymer Science and Technology*, Vol. 3, pp 325 to 354, 1964, published by Interscience Publishers, Inc., New York.

Additional semipermeable polymer include cellulose acetaldehyde dimethyl cellulose acetate; cellulose acetate ethylcarbamate; cellulose acetate methylcarbamate; cellulose dimethylaminoacetate; a cellulose composition comprising cellulose acetate and hydroxypropyl methylcellulose; a composition comprising cellulose acetate and cellulose acetate butyrate; a cellulose composition comprising cellulose acetate butyrate and hydroxypropyl methylcellulose; semipermeable polyamides; semipermeable polyurethanes; semipermeable polysulfanes; semipermeable sulfonated polystyrenes, cross-linked, selectively semipermeable polymers formed by the coprecipitation of a polyanion and a polycation as disclosed in U.S. Pat. Nos. 3,173,876; 3,276,586; 3,541,005; 3,541,006, and 3,546,142; selectively semipermeable silicon rubbers; semipermeable polymers as disclosed by Loeb and Sourirajan in U.S. Pat. No. 3,133,132; semipermeable polystyrene derivatives; semipermeable (polysodium-styrenesulfonate); semipermeable poly(vinylbenzyltrimethyl) ammonium chloride; semipermeable polymer exhibiting a fluid permeability of $10^{-1}$ to $10^{-7}$ (cc.mil/cm2 hr.atm) expressed as per atmosphere of hydrostatic or osmotic pressure difference across a semipermeable wall. The polymers are known to the art in U.S. Pat. Nos. 3,845,770, 3,916,899, and 4,160,020, and in *Handbook of Common Polymers*, by Scott, J. R. . and Roff, W. J., 1971, published by CRC Press, Cleveland, Ohio.

Semipermeable wall 12 also can comprise a flux regulating agent. The flux regulating agent is a compound added regulating the fluid permeability of flux through the semipermeable wall. The flux regulating agent can be a flux enhancing agent or a flux decreasing agent. The agent can be preselected to increase or decrease the liquid flux. Agents that produce a marked increase in permeability to fluid such as water, are often essentially hydrophilic, while those that produce a marked decrease to fluids such as water, are essentially hydrophobic. The amount of regulator in the wall when incorporated therein generally is from about 0.01% to 20% by weight or more. The flux regulator agents in one embodiment that increase flux include polyhydric alcohols, polyalkylene glycols, polyalkylenediols, polyesters of alkylene glycols, and the like. Typical flux enhancers include polyethylene glycol 300, 400, 600, 1500, 4000, 6000 and the like; low molecular weight glycols such as polypropylene glycol, polybutylene glycol and polyamylene glycol: the polyalkylenediols such as poly(1,3-propanediol), poly(1,4-butanediol), poly(1,6-hexanediol), and the like; aliphatic diols such as 1,3-butylene glycol, 1,4-pentamethylene glycol, 1,4-hexamethylene glycol, and the like; alkylene triols such as glycerine, 1,2,3-butanetriol, 1,2,4-hexanetriol, 1,3,6-hexanetriol and the like; ester such as ethylene glycol dipropionate, ethylene glycol butyrate, butylene glycol dipropionate, glycerol acetate esters, and the like. Representative flux decreasing agents include phthalates substituted with an alkyl, an alkoxy or with both an alkyl and alkoxy group such as diethyl phthalate, dimethoxyethyl phthalate, dimethyl phthalate, and [di(2-ethylhexyl) phthalate]; aryl phthalates such as triphenyl phthalate, and butyl benzyl phthalate; insoluble salts such as calcium sulphate, barium sulphate, calcium phosphate, and the like; insoluble oxides such as titanium oxide; polymers in powder, granule and like form such as polystyrene, polymethylmethacrylate, polycarbonate, and polysulfone; esters such as citric acid esters esterified with long chain alkyl groups; inert and substantially water impermeable fillers; resins compatible with cellulose based wall forming materials, and the like.

Other materials that can be used to form the semipermeable wall for imparting flexibility and elongation properties to the wall, for making the wall less to non-brittle and to render tear strength, include phthalate plasticizers such as dibenzyl phthalate, dihexyl phthalate, butyl octyl phthalate, straight chain phthalates of six to eleven carbons, diisononyl phthalate, diisodecyl phthalate, and the like. The plasticizers include nonphthalates such as triacetin, dioctyl azelate, epoxidized tallate, triisoctyl trimellitate, triisononyl trimellitate, sucrose acetate isobutyrate, epoxidized soybean oil, and the like. The amount of plasticizer in a wall when incorporated therein is about 0.01% to 20% by weight, or higher.

Expandable layer 18 that has a shape that corresponds to the internal shape of capsule wall 14 and compartment 15 is made from a hydrogel composition. The hydrogel composition is noncross-linked or optionally cross-linked and it possesses osmotic properties, such as the ability to imbibe an exterior fluid through semipermeable wall 12, and exhibit an osmotic pressure gradient across semipermeable wall 12 against a fluid outside delivery system 10. The materials used for forming the swellable, expandable inner layer and the plug, are polymeric materials neat, and polymeric materials blended with osmotic agents that interact with water or a biological fluid, absorb the fluid and swell or expand to an equilibrium state. The polymer exhibits the ability to retain a significant fraction of imbibed fluid in the polymer molecular structure. The polymers in a preferred embodiment are gel polymers that can swell or expand to a very high degree, usually exhibiting a 2 to 50 fold volume increase. The swellable, hydrophilic polymers, also known a osmopolymers can be noncross-linked or lightly cross-linked. The cross-links can be covalent or ionic bonds with the polymer possessing the ability to swell in the presence of fluid, and when cross-linked it will not dissolve in the fluid. The polymer can be of plant, animal or synthetic origin. Polymeric materials useful for the present purpose include poly(hydroxyalkyl methacrylate) having a molecular weight of from 5,000 to 5,000,000; poly(vinylpyrrolidone) having a molecular weight of from 10,000 to 360,000; anionic and cationic hydrogels; cationic hydrogels; poly(electrolyte) complexes; poly(vinylalcohol) having a low acetate residual; a swellable mixture of agar and carboxymethyl cellulose; a swellable composition comprising methyl cellulose mixed with a sparingly cross-linked agar; a water-swellable copolymer produced by a dispersion of finely divided copolymer of maleic anhydride with styrene, ethylene, propylene, or isobutylene; water swellable polymer of N-vinyl lactams; and the like.

Other gelable, fluid imbibing and retaining polymers useful for forming the hydrophilic, expandable push member include pectin having a molecular weight ranging from 30,000 to 300,000; polysaccharides such as agar, acacia, karaya, tragacanth, algins and guar; Carbopol ® acidic carboxy polymer and its salt derivatives; polyacrylamides; water-swellable indene maleic anhydride polymers; Good-rite ® polyacxylic acid having a molecular weight of 80,000 to 200,000; Polyox ® polyethylene oxide polymers having a molecular weight of 100,000 to 5,000,000; starch graft copolymers; Aqua-Keep ® acrylate polymers with water absorbability of about 400 times its original weight; diesters of polyglucan; a mixture of cross-linked polyvinyl alcohol and poly(N-vinyl-2-pyrrolidone); zein available as prolamine; poly(ethylene glycol) having a molecular weight of 4,000 to 100,000; and the like. In a preferred embodiment, the expandable member is formed from polymers and polymeric compositions that are thermoformable. Representative polymers possessing hydrophilic properties are known in U.S. Pat. Nos. 3,865,108; 4,002,173; 4,207,893; 4,327,725, and in *Handbook of Common Polymers*, by Scott and Roff, published by Cleveland Rubber Company, Cleveland, Ohio.

The osmotically effective compound that can be blended homogeneously or heterogeneously with the swellable polymer, to form a push member, are the osmotically effective solutes that are soluble in fluid imbibed into the swellable polymer, and exhibit an osmotic pressure gradient across the semipermeable wall against an exterior fluid. Osmotically effective compounds are known also as osmagents. Osmotically effective osmagents useful for the present purpose include magnesium sulfate, magnesium chloride, sodium chloride, lithium chloride, potassium sulfate, sodium sulfate, mannitol, urea, sorbitol, inositol, succrose, glucose, and the like. The osmotic pressure in atmospheres, ATM, of the osmagents suitable for the invention will be greater than zero ATM, generally from eight ATM up to 500 ATM, or higher.

The swellable, expandable polymer, in addition to providing a driving source for delivering a beneficial agent from the dispenser 10, further serves to function as a supporting matrix for an osmotically effective solute. The osmotic solute can be homogeneously or heterogeneously blended with the polymer to yield the desired expandable member 18. The composition in a presently preferred embodiment comprises at least one polymer and at least one osmotic solute. Generally, a composition will comprise about 20% to 90% by weight of polymer and 80% to 10% by weight of osmotic solute, with a presently preferred composition comprising 35% to 75% by weight of polymer and 65% to 25% by weight of osmotic solute.

The thermo-responsive composition 16, containing agent 17 homogeneously or heterogeneously dispersed or dissolved therein, is formed in a presently preferred embodiment of a heat sensitive, hydrophilic or hydrophobic material that exhibits solid-like properties at room temperature of 21° C., and within a few centigrade degrees thereof, and exhibits, in a preferred embodiment, a melting point that approximates mammalian body temperatures of 37° C., and with a few centigrade degrees thereof. The present invention uses the phrases "melting point", "softening point", "pour point", or "liquifies" to indicate the temperature at which the thermo-responsive composition melts, undergoes dissolution, or forms a paste-like ribbon, dissolves to form a dispensable carrier so it can be used for dispensing agent 17 from dispenser 10.

The term "thermo-responsive" as used for the purpose of this invention includes thermoplastic compositions capable of softening, or becoming dispensable in response to heat and hardening again when cooled. The term also includes thermotropic compositions capable of undergoing change in response to the application of energy in a gradient manner. These are temperature sensitive in their response to the application or withdrawl of energy. The term "thermo-responsive" as used for the purpose of this invention in a preferred embodiment denotes the physical-chemical property of a composition agent carrier to exhibit solid, or solid-like properties at temperatures up to 31° C., and become fluid, semisolid, or viscous when disturbed by heat at temperatures from 31° C., usually in the range of 31° C. to 45° C. The thermo-responsive carrier is heat-sensitive and preferably anhydrous and it has the property of melting, dissolving, undergoing dissolution, softening, or liquifying at the elevated temperatures, thereby making it possible for the dispenser 10 to deliver the thermo-responsive carrier with the beneficial agent 17 homogeneously or heterogeneously blended therein. The thermoresponsive carrier can be lipophilic, hydrophilic or hydrophobic. Another important property of the carrier is its ability to maintain the stability of the agent contained therein during storage and during delivery of the agent. Representative thermo-responsive compositions and their melting points are as follows: cocoa butter, 32°-34° C.; cocoa butter plus 2% beeswax, 35°-37° C.; propylene glycol monostearate and distearate, 32°-35° C.; hydrogenated oils such as hydrogenated vegetable oil, 36°-37.5° C.; 80% hydrogenated vegetable oil and 20% polysorbate 60, 36°-37° C.; 77.5% hydrogenated vegetable oil, 20% sorbitan trioleate and 2.5% beeswax, 35°-36° C.; 72.5% hydrogenated vegetable oil, 20% sorbitan trioleate, 2.5% beeswax and 5.0% distilled water, 37°-38° C.; mono-, di-, and triglycerides of acids having from 8-22 carbon atoms including saturated and unsaturated acids such as palmitic, stearic, oleic, lineolic, linolenic and archidonic; glycerides of fatty acids having a melting point of at least 32° C. such as monoglycerides, diglycerides and triglycerides of vegetable fatty acids having 10 to 18 carbon atoms obtained from coconut oil, olive oil and the like; partially hydrogenated cottonseed oil, 35°-39° C.; hardened fatty alcohols and fats, 33°-36° C.; hexadienol and hydrous lanolin triethanolamine glyceryl monostearate, 38° C.; eutectic mixtures of mono-, di-, and triglycerides, 35°-39° C.; Witepsol ® #15, triglyceride of saturated vegetable fatty acid with monoglycerides, 33.5°-35.5° C.; Witepsol ® H32 free of hydroxyl groups, 31°-33° C.; Witepsol ® W25 having a saponification value of 225-240 and a melting point of 33.5°-35.5° C.; Witepsol ® E75 having a saponification value of 220-230 and a melting point of 37°-39° C.; a polyalkylene glycol such as polyethylene glycol 1000, a linear polymer of ethylene oxide, 38°-41° C.; polyethylene glycol 1500, melting at 38°-41° C.; polyethylene glycol monostearate, 39°-42.5° C.; 33% polyethylene glycol 1500, 47% polyethylene glycol 6000 and 20% distilled water, 39°-41° C.; 30% polyethylene glycol 1500, 40% polyethylene glycol 4000 and 30% polyethylene glycol 400, 33°-38° C.; mixture of mono-, di-, and triglycerides of saturated fatty acid having 11 to 17 carbon atoms, 33°-35° C.; block polymer of 1,2-butylene oxide and ethylene oxide; block polymer of propylene oxide and ethylene oxide; block polymer of polyoxyalkylene and propylene glycol, and the like. The thermo-responsive composition is a means for storing a beneficial agent in a solid composition at a temperature of 20°-32° C., maintaining an immiscible boundary at the swelling composition interface, and for dispensing the agent in a flowable composition at a temperature greater than 32° C., and preferably in the range of 32°-40° C. The thermo-responsive composition on being dispensed into a biological environment are easily excreted, metabolized, assimilated, or the like, for effective use of the beneficial agent.

The dense member 20, also referred to as densifier 20, used in delivery system 10 is dense enough to retain system 10 in the rumen-reticular sac of a ruminant. Dense member 20 lets system 10 remain in the rumen over a prolonged period of time rather than letting it pass into the alimentary tract and be eliminated therefrom. As system 10 remains in the rumen, beneficial active agent 17 is delivered by system 10 at a controlled rate to the ruminant over time. Generally, dense member 20 will have a density of from about 0.8 to 8, or higher, with the density in a presently preferred embodiment exhibiting a specific gravity of from 2.2 to 7.6. For the ruminants, cattle and sheep, it is presently preferred dense member 20 exhibit a density such that there is a resulting system density of about 3. Materials that have a density that can be used for forming dense member 20 include iron, iron shot, iron shot coated with iron oxide, iron shot magnesium alloy, steel, stainless steel, copper oxide, a mixture of cobalt oxide and iron powder, and the like. Dense member 20 in delivery system 10 can embrace different embodiments. For example, dense member 20 as seen in FIG. 2 is machined or cast as a single, solid piece made of stainless steel having a density of 7.6. The solid member is made having a curved shape that corresponds to the internal shape of system 10. The solid member has an axially aligned bore that extends through the length of the unit member. In another embodiment, dense member 20 can compose a plurality of dense pellets. In this latter embodiment, the pellets are used as dense member 19 in FIG. 3.

The term "beneficial agent" as used herein includes medicines or drugs, nutrients, vitamines, food supplements and other agents that benefit a ruminant animal. The beneficial agent can be insoluble to very soluble in the temperature sensitive material housed in the delivery system. The amount of agent present in a delivery system can be from 10 ng to 40 g or more. The delivery system can house various amounts of the beneficial agent, for example, 75 ng, 1 mg, 5 mg, 100 mg, 250 mg, 750 mg, 1.5 mg, 2 g, 5 g, 10 g, 25 g, and the like. A single delivery system can be administered to a ruminant, or more than one delivery system can be administered to a ruminant during a therapeutic program. Delivery systems can be provided that have a rate of release from 5 micrograms to 5 grams per day, or higher.

Representative of beneficial medicaments that can be dispensed using the delivery system of this invention include anthelmintics such as mebendazole, levamisole, albendazole, cambendazole, fenbendazole, parbendazole, oxfendazole, oxibendazole, thiabendazole, tichlorfon, praziquantel, morantel and pyrantel, and the like; antiparasitic agents such as avermectin and ivermectin, as disclosed in U.S. Pat. Nos. 4,199,569 and 4,389,397 both assigned to Merck & Co., and in Science, Vol. 221, pp 823-828, 1983, wherein said ivermectin antiparasitic drug are disclosed as useful for aiding in controlling commonly occurring infestations in animals, such as roundworms, lung worms and the like; and said ivermectin also being used for the management of insect infestations such as grub, lice, mange mite, and the like, with delivery system administering from 5 micrograms per kilogram per day, (5 μg/kg/d), to 250 milligrams per day (250 mg/kg/d), to cattle for establishing avermectin, including ivermectin, blood levels; antimicrobial agents such as chlortetracycline, oxytetracycline, tetracycline, streptomycin, dihydrostreptomycin, bacitracins, erythromycin, ampicillins, penicillins, cephalosporins, and the like; sulfa drugs such as sulfamethazine, sulfathiazole, and the like; growth-stimulants such as Monensin ® sodium and Elfazepam ®; defleaing agents such as dexamethazone and flumethazone; rumen fermentation manipulators and ionophores such as lasalocid, virginamycin and ronnel; minerals and mineral salts; anti-bloat agents such as organopoly siloxanes; hormone growth supplements such as stilbestrol; vitamins, antienteritis agents such as furazolidone; nutritional supplements such as lysine monohydrochloride, methionine, magnesium carbonate, and the like.

The semipermeable wall forming composition can be applied to the exterior surface of the capsule in laminar arrangement by molding, air spraying, dipping or brushing with a semipermeable wall forming composition. Other and presently preferred techniques that can be used for applying the semipermeable wall are the air suspension procedure and the pan coating procedures. The air procedure consists in suspending and tumbling the capsule arrangement in a current of air and a semipermeable wall forming composition until the wall surrounds and coats the capsule member. The procedure can be repeated with a different semipermeable wall forming composition to form a semipermeable laminated wall. The air suspension procedure is described in U.S. Pat. No. 2,799,241; *J. Am. Pharm. Assoc.*, Vol. 48, pp 451 to 459, 1979; and ibid, Vol. 49, pp 82 to 84, 1960. Other standard manufacturing procedures are described in *Modern Plastics Encyclopedia*, Vol. 46, pp 62 to 70, 1969; and in *Pharmaceutical Sciences*, by Remington, 14th Edition, pp 1626 to 1678, 1970, published by Mack Publishing Co., Easton, Pa.

Exemplary solvents suitable for manufacturing the semipermeable wall include inert inorganic and organic solvents that do not adversely harm the materials, the capsule wall, the beneficial agent, the thermo-responsive composition, the expandable member, the dense member, and the final dispenser. The solvents broadly include members selected from the group consisting of aqueous solvents, alcohols, ketones, esters, ethers, aliphatic hydrocarbons, halogenated solvents, cycloaliphatics, aromatics, heterocyclic solvents and mixtures thereof. Typical solvents include acetone, diacetone alcohol, methanol, ethanol, isopropyl alcohol, butyl alcohol, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, carbon tetrachloride, nitroethane, nitropropane, tetrachloroethane, ethyl ether, isopropyl ether, cyclohexane, cyclo-octane, benzene, toluene, naphtha, 1,4-dioxane, tetrahydrofuran, diglyme, water, and mixtures thereof such as acetone and water, acetone and methanol, acetone and ethyl alcohol, methylene dichloride and methanol, and ethylene dichloride and methanol. Generally, for the present purpose the semipermeable wall is applied at a temperature a few degrees less than the melting point of the thermo-responsive composition. Or, the thermoplastic composition can be loaded into the dispenser after applying the semipermeable wall.

The expression, "means in the wall for releasing a beneficial agent formulation" includes at least one, or a plurality of preformed or formed in the environment of use, orifices or passageways suitable for releasing the beneficial agent formulation from the dispenser. The agent exit mean in the wall embraces also aperture, bore, pore, porous element, hollow fiber, leachable element, dissolvable element, erodible element, hollow fiber, capillary tube, and the like. The agent exit means can be formed by mechanical drilling, by laser drilling, by eroding an erodible element in the wall, by dissolving or leaching a pore former such as sorbitol from a wall forming polymer composition thereby providing at least one pore of governed porosity, and the like. The exit releasing means can be a microporous insert or a microporous overlay. The exit means can be present in the wall formed in at least a part of a semipermeable material, or the exit means can be through the semipermeable wall and the capsule wall. The exit means in one wall or both walls also can be formed by bursting or in response to pressure, especially when the dispenser is in operation in the environment of use. A detailed description of orifices and passageways maximum and minimum dimensions is disclosed by Theeuwes and Higuchi in U.S. Pat. Nos. 3,845,770 and 3,916,899. A detailed description of an osmotically operated system with an agent releasing wall comprising and at least one pore, or a multiplicity of agent releasing pores of regulated porosity formed by leaching and the like, is discussed by Ayer and Theeuwes in U.S. Pat. Nos. 4,200,098 and 4,285,987. A dispenser of similar structure comprising a size-controlled porous releasing wall comprising a porous polymer and the pore former hexanehexol or sorbitol is disclosed by Theeuwes in U.S. Pat. No. 4,235,236.

DESCRIPTION OF EXAMPLES OF THE INVENTION

The following examples are merely illustrative of the present invention and they should not be considered as limiting the scope of the invention in any way, as these examples and other equivalents thereof will become apparent to those versed in the art in the light of the present disclosure, the drawings and the accompanying claims.

EXAMPLE 1

A delivery system manufactured in the shape of a dispenser for the controlled delivery of ivermectin is made as follows: first, 193 g of Butronic ® L-1 polyol, a block polymer formed by the polymerization of 1,2-butylene oxide to which ethylene oxide is added, as reported in *Cosmetics and Toiletries*, Vol. 97, pp 61–66, 1982, which polymer flow at a pour point of 39° C., is melted at 55° C. and then 13.98 g of ivermectin is added thereto using a high sheer ultrasonic mixer. The resulting mixture is placed in a vacuum oven at 55° C. and the pressure reduced to less than 10 mm of mercury. The ivermectin Butronic ® composition is allowed to remain in the vacuum for a period of about 10 minutes, for removing entrapped air. Next, 4 g of the resulting thermoplastic drug formulation is poured into a ½ oz. gelatin capsule that is previously charged with a 33 g stainless steel density member having a bore therethrough. Then, an expandable driving member comprising 2.1 g of sodium chloride and 4.9 g of the sodium salt of polyacrylic acid available as Carbopol ® 934P is compressed into a tablet. The tablet is formed using a 18.2 mm tableting tool and 3½ tons of compression force. The tablet has a final shape that corresponds to the internal shape of the opening of the capsule. The tablet member then is inserted into the opened end of the capsule until contact is made with the drug polyol formation. Next, the capsule is coated in a pan coater with a rate controlling wall comprising 1.8 g of 91% cellulose acetate butyrate and 9% polyethylene glycol 400. The wall is coated from a 5% wt/wt solution in methylene chloride methanol 90:10 v/v solvent system. The wall coated delivery systems then are dried at 30° C. for 24 hours. Next, a 30 mil exit passageway is drilled through the semipermeable wall using a high speed mechanical drill for communicating the passageway with the bore. The passageway bore arrangement establishes communication with the heat-responsive drug formulation for delivering it from the delivery system. The dispenser made according to this example has an average release rate of 0.5 mg per hour over a 480 hr period of time.

EXAMPLE 2

A delivery system is made according to the procedure set forth in Example 1, with the conditions as set forth, except that in this example, the heat-responsive composition comprises 46.6 g of ivermectin and 200 g of polyethylene glycol 400 distearate, and the expandable-swellable composition comprises 70% by weight of poly(ethylene oxide) having a molecular weight of 3,000,000 and 30% by weight of sodium chloride.

EXAMPLE 3

A dispenser system is prepared as follows: first, the body section of a capsule is positioned with its mouth in an upright position, and a dense stainless steel element inserted into the hemispherical end of the capsule. The dense element is machined and its shape matches the internal shape of the capsule. Next, a layer of an expandable-swellable composition is charged on top of the dense element. The composition comprises 25% by weight of sodium chloride and 75% by weight of poly-(ethylene oxide) having a molecular weight of 200,000. The expandable forming ingredients are blended in a commercial blender with heat for 20 minutes to yield a homogeneous composition. The heated composition is charged into the capsule forming a layer that occupies about ⅓ of the capsule. Next, a heat-sensitive drug formulation comprising an eutectic mixture of 77% neutral fat having a melting point of 35°-37° C. and 19.5% paraffin having a melting point of 52° C. is heated and 3.5% levamisole is added thereto. Then, the heated mixture is cooled to about 40° C. and injected into the capsule in contacting relation with the expandable layer, and the capsule allowed to cool to room temperature. Then, a solution of cellulose acetate, 15 wt %, with an acetyl content of 39.8%, is prepared in a methylene chloride methanol solvent system and the capsule coated with a semipermeable wall. The wall is applied by dipping it into the coating solution for 15 times, first for a 5 second dip, then for two 10 second dips, then for a 30 second dip and then for 1 minute per dip, with an intervening 5 minute drying period. Following the dipping the delivery dispenser is dried at room temperature, 72° F., about 22° C., for 5 days. The procedure applies about a 2 mm thick semipermeable wall. A passageway is laser drilled through the semipermeable wall connecting the exterior of the dispenser with the heat sensitive drug formulation for releasing it at a controlled rate over time.

EXAMPLE 4

A dispensing system for delivering beneficial nutrients to warm-blooded ruminants is prepared a follows: first, a mold having a shape and configuration corresponding to the internal diameter and the hemispherical closed end of a capsule, is filled with an expandable forming composition comprising 30 parts of ethyleneglycol monomethacrylate containing 0.12 parts of ethyleneglycol dimethacrylate and 10 parts of a 0.13% aqueous solution of sodium disulfate in aqueous ethanol. The composition polymerizes at 30° C., and after 20 minutes following equilibrium to room temperature, the solid layer is removed from the mold. The solid expandable layer then is inserted, through the mouth of the capsule into the hemispherical area of the capsule. Next, a dense member made of stainless steel and machined in the shape of a tablet is placed inside the capsule in contacting laminar arrangement with the expandable layer. Next, the remainder of the capsule is filled with a melted composition comprising 2.5% L-lysine HCl, 1.5% DLmethionine, 21% glycergelatin and 75% theobromo oil, a glyceride of stearic acid, palmitic acid and lauric acid, to form on cooling to room temperature the thermo-responsive composition in laminar position with the dense member. Next, the filled capsule is coated with a surrounding wall comprising cellulose acetate containing 10% polyethylene glycol 400. The semipermeable wall is applied in a pan type Hi-coater. The solvent used for forming the wall consists essentially of methylene chloride and methanol 95 parts by weight to 5 parts by weight. A 12 mil (0.30 mm) thick wall of cellulose acetate butyrate is applied to the exterior surface of the capsule. Finally, a passageway is laser drilled through the semipermeable wall communicating with the heat-responsive nutrient containing composition for its delivery to the environment of use.

EXAMPLE 5

Figure 12:
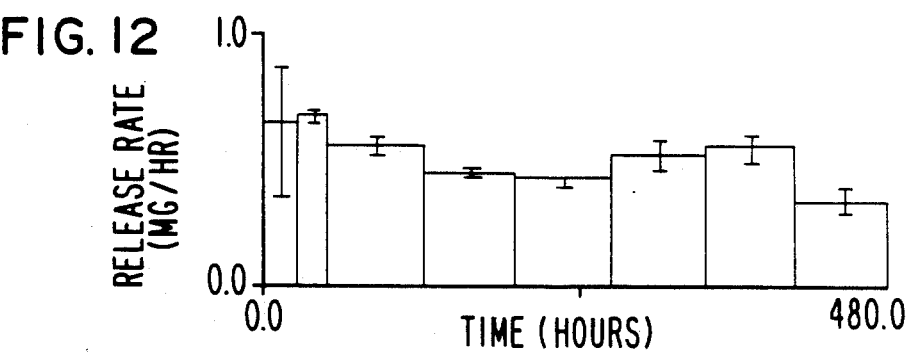
FIG. 12 depicts the amount of a beneficial agent released over time by a system provided by the invention.
Figure 13:
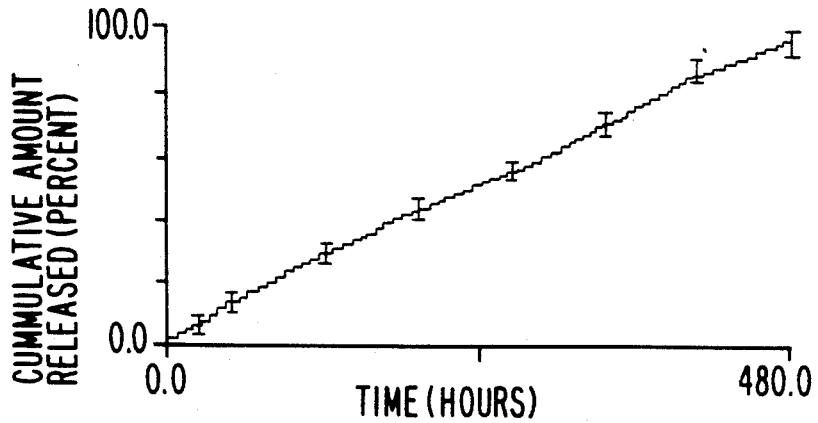
FIG. 13 depicts the cumulative amount of beneficial agent released by a delivery system over a prolonged period of time.

A delivery system is made according to the procedure set forth in Example 1, with the conditions and materials as set forth, except that in this example a varying rate controlling wall thickness of cellulose acetate butyrate and polyethylene glycol 400 was applied to the system. The thickness of the rate controlling wall varied from 30 mil (0.76 mm) at the end distant from the passageway in a uniform taper to 15 mil (0.38 mm) adjacent to the density member. Accompanying FIG. 12 depicts the amount of ivermectin antiparasitic released from the system over a prolonged period of 480 hours, and FIG. 13 depicts the cumulative amount of ivermectin released over the 480 hour period. The bars represent the minimum and maximum variation for the release rate at the time of measurement.

EXAMPLE 6

A delivery system is made according to the procedure as set forth in Example 1, with all conditions and materials as previously described, except for the semipermeable wall that comprises 50% cellulose acetate butyrate, 45% poly(sulfone) and 5% citroflex citric acid ester selected from the group consisting of acetyl tributyl citrate and acetyl tri-2-ethylhexyl citrate.

EXAMPLE 7

A delivery system is made according to the procedure as set forth in Example 1, with all conditions as described except that the semipermeable wall comprises 80% cellulose acetate butyrate and 20% poly(sulfone), or 20% cellulose acetate butyrate and 80% poly(sulfone).

A presently preferred embodiment of the invention pertains to a method of delivering a beneficial agent by formulating a heat-sensitive composition containing the beneficial agent and then delivering the beneficial agent. An embodiment of the invention pertains also to a method for administering a beneficial drug at a controlled rate to the rumen of a ruminant, which method comprises the steps of: (A) admitting into rumen a dispensing device comprising: (1) an outer wall formed of a semipermeable polymeric composition permeable to the passage of fluid and substantially impermeable to the passage of drug, the wall surrounding (2) an internal lumen containing a layer of a beneficial drug formulation comprising a dosage unit amount of drug for preforming a therapeutic program in a heat-sensitive, pharmaceutically acceptable carrier that melts at body temperature and is a means for transporting the drug from the dispenser; (3) a layer of an expandable member in the lumen; (4) a layer of a dense member for maintaining the dispenser in the rumen over a prolonged period of time; and (5) an orifice through the semipermeable wall communicating with the heat-sensitive drug formulation; (B) imbibing fluid through the semipermeable wall at a rate determined by the permeability of the semipermeable wall and the osmotic pressure gradient across the semipermeable wall causing the layer of expandable hydrogel to expand and swell; (C) melting the drug formulation to form a flowable formulation; and (D) delivering the beneficial drug formulation from the compartment by the expandable layer continually expanding against the melting formulation causing the formulation to be dispensed in a therapeutically effective amount through the orifice at a controlled rate to the rumen over a prolonged period of time.

Figure 14:
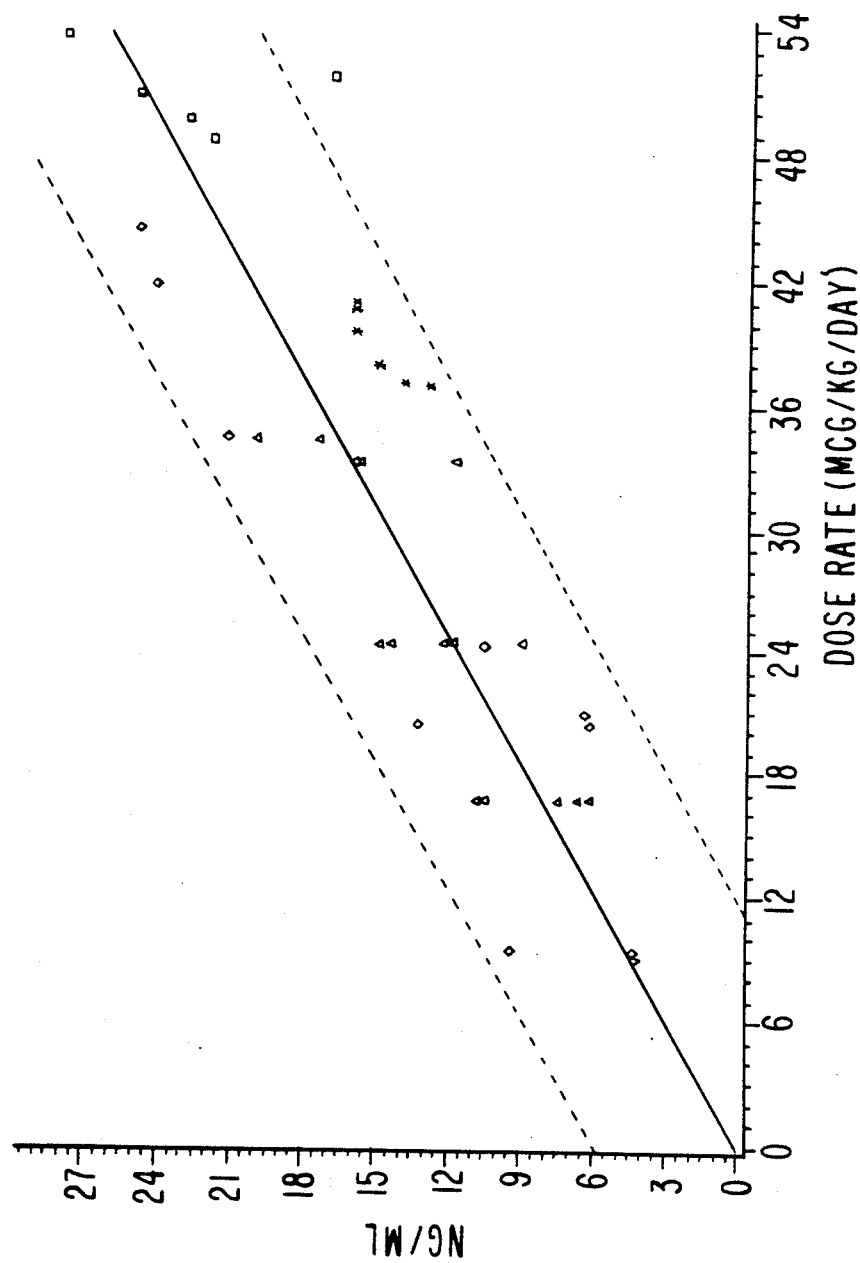
FIG. 14 is a graph that depicts the mean steady state plasma level as a function of dose rate.

The dispensing device provided by the invention are used, for example, for administering ivermectin to a warm-blooded animal at the rate of 5 µg/kg/d to 250 µg/kg/d, and more, preferably at the rate of 10 µg/kg/d to 50 µg/kg/d for establishing plasma levels of about 2 ng/ml to 100 ng/ml for substantially eliminating endoparasites in cattle, and for establishing plasma levels of 10 ng/ml to 200 ng/ml for substantially eliminating ectoparasites in cattle. The accompanying FIG. 14 presents mean steady state plasma levels as a function of dose rates. The solid line denotes the regression line based on the data. The hatched lines denote the 95% confidence interval about the regression line. The squares, triangles, diamonds and horizontal-vertical intersecting lines indicate plasma measured points. The dispensing device provides prolonged administration of the medication to the animal accompanied by a reduction in the frequency of administration with the maintenance of a relatively constant drug concentration in the blood, leading to a more uniform pharmacological response.

Inasmuch as the foregoing specification comprises preferred embodiments of the invention, it is understood that variation and modifications may be made herein in accordance with the inventive principles disclosed, without departing from the scope of the invention.

We claim:

1. A method for producing an avermectin blood level of 2 ng/ml in an animal for the management of infestation, which method comprises:
   (a) admitting into the animal a dispenser, the dispenser comprising:
      (1) a wall that surrounds and defines an internal lumen;
      (2) means in the lumen comprising from 10 ng to 40 g of avermectin, said means comprising a heat responsive composition that absorbs heat form the animal and thereby forms a dispensable composition comprising avermectin;
      (3) means in the lumen for occupying more space in the lumen and for exerting pressure against the means comprising avermectin for urging avermectin from the dispenser;
      (4) exit means in the dispenser communicating with the lumen for delivering avermectin from the dispenser; and,
   (b) administering the avermectin by the means absorbing heat and forming a dispensable composition and by the means for occupying space, occupying more space and exerting pressure against the dispensable composition, whereby avermectin is delivered through the exit means in a beneficially effective amount to the animal for producing the avermectin blood level over time.

2. The method for producing the avermectin blood level according to claim 1, wherein the method produces a continuous avermectin blood level.

3. The method for producing an ivermectin blood concentration according to claim 2, wherein the ruminant is a sheep.

4. The method for producing an ivermectin blood concentration according to claim 2, wherein the ruminant is a cow.

5. The method for producing an ivermectin blood concentration according to claim 2, wherein the ruminant is a steer.

6. The method for producing an ivermectin blood concentration according to claim 2, wherein the method produces a continuous ivermectin blood concentration.

7. The method for producing an ivermectin blood concentration according to claim 2, wherein the method produces a pulsatile ivermectin blood concentration.

8. The method for producing an ivermectin blood concentration according to claim 2, wherein the exit means comprises at least one passageway.

9. The method for producing an ivermectin blood concentration according to claim 2, wherein the exit means comprises at least one passageway formed when the dispenser is in use.

10. The method for producing the avermectin blood level according to claim 1, wherein the method produces a pulsatile avermectin blood level.

11. The method for producing the avermectin blood level according to claim 1, wherein the exit means comprises at least one passageway.

12. The method for producing the avermectin blood level according to claim 1, wherein the exit means comprises at least one passageway formed when the dispenser is in use.

13. A method for producing an ivermectin blood concentration of 10 ng/ml to 200 ng/ml in a ruminant for the management of an infestation, which method comprises:
   (a) admitting orally into the a ruminant a dispenser, said dispenser comprising:
      (1) a wall that surrounds and defines an internal lumen;
      (2) means in the lumen comprising from 10 ng to 25 g of ivermectin, said means comprising a heat responsive composition that absorbs heat from the ruminant and thereby forms a dispensable composition comprising ivermectin;
      (3) means in the lumen for absorbing and imbibing fluid from the ruminant for continuously occupying space in the lumen and for exerting pressure against the means comprising ivermectin for urging ivermectin from the dispenser;

(4) exit means in the dispenser communicating with the lumen for delivering ivermectin from the dispenser; and, (b) administering the ivermectin by the means absorbing heat and forming a dispensable composition and by the means for occupying space, occupying more space thereby exerting pressure against the dispensable composition, whereby ivermectin is delivered through the exit means in a beneficially effective amount to the ruminant to produce an ivermectin blood concentration of 10 ng/ml to 200 ng/ml over a prolonged period of time.

14. A method of treating a parasitic infection in a warm-blooded animal suffering from such an infection, which method comprises:

(a) administering to the animal a therapeutically effective dose of avermectin by admitting into the animal a delivery system, said delivery system comprising:

(1) a wall that surrounds and defines an internal compartment;

(2) a dosage unit amount of avermectin in the compartment in contacting relationship with means for absorbing heat from the animal for forming a dispensable carrier for dispensing the avermectin from the delivery system;

(3) means in the compartment for using fluid that enters the compartment for increasing in volume for applying pressure against the dispensable carrier;

(4) exit means in the delivery system that connects the compartment with the exterior of the delivery system for dispensing avermectin from the delivery system; and, (b) administering the avermectin by the means absorbing heat and forming a dispensable carrier, and by the means using fluid and increasing in volume for applying pressure against the dispensable carrier, whereby the avermectin is administered through the exit means in a therapeutically effective dose to the animal over time.

15. The method of treating a parasitic infection in the warm-blooded animal according to claim 14, wherein the avermectin is ivermectin.

* * * * *

UNITED STATES PATENT AND TRADEMARK OFFICE
CERTIFICATE OF CORRECTION

PATENT NO. : 4,612,186

DATED : September 16, 1986

INVENTOR(S) : James B. Eckenhoff, Richard Cortese and Felix A. Landrau

It is certified that error appears in the above-identified patent and that said Letters Patent is hereby corrected as shown below:

Column 17, line 58; Claim 1:

of 2 ng/ml should read-- of 2 ng/ml to 100 ng/ml---

Signed and Sealed this

Sixteenth Day of December, 1986

*Attest:*

DONALD J. QUIGG

*Attesting Officer*         *Commissioner of Patents and Trademarks*